US011045450B2

(12) United States Patent
Sutherland et al.

(10) Patent No.: US 11,045,450 B2
(45) Date of Patent: Jun. 29, 2021

(54) DRUG COMPOSITIONS

(71) Applicant: Adamis Pharmaceuticals Corporation, San Diego, CA (US)

(72) Inventors: David Clayton Sutherland, Little Rock, AR (US); James Kyle Zorn, Lexington, KY (US); Dennis J. Carlo, San Diego, CA (US)

(73) Assignee: Adamis Pharmaceuticals Corporation, San Diego, CA (US)

( * ) Notice: Subject to any disclaimer, the term of this patent is extended or adjusted under 35 U.S.C. 154(b) by 0 days.

(21) Appl. No.: 16/560,806

(22) Filed: Sep. 4, 2019

(65) Prior Publication Data

US 2019/0388396 A1 Dec. 26, 2019

Related U.S. Application Data

(60) Continuation of application No. 15/914,804, filed on Mar. 7, 2018, now Pat. No. 10,441,575, which is a division of application No. 15/675,435, filed on Aug. 11, 2017, now Pat. No. 10,137,111.

(60) Provisional application No. 62/373,871, filed on Aug. 11, 2016.

(51) Int. Cl.
| | | |
|---|---|---|
| A61K 31/4184 | (2006.01) | |
| A61K 45/06 | (2006.01) | |
| A61K 31/4439 | (2006.01) | |
| A61K 9/16 | (2006.01) | |
| A61K 47/38 | (2006.01) | |
| A61K 9/10 | (2006.01) | |
| A61K 9/14 | (2006.01) | |
| C08L 1/28 | (2006.01) | |
| C01D 5/14 | (2006.01) | |
| C01D 7/10 | (2006.01) | |
| C08B 3/06 | (2006.01) | |

(52) U.S. Cl.
CPC ............ *A61K 31/4184* (2013.01); *A61K 9/10* (2013.01); *A61K 9/145* (2013.01); *A61K 9/1641* (2013.01); *A61K 9/1652* (2013.01); *A61K 31/4439* (2013.01); *A61K 45/06* (2013.01); *A61K 47/38* (2013.01); *A61K 2300/00* (2013.01); *C01D 5/14* (2013.01); *C01D 7/10* (2013.01); *C08B 3/06* (2013.01); *C08L 1/286* (2013.01)

(58) Field of Classification Search
CPC ...... A61K 31/4184; A61K 9/10; A61K 9/145; A61K 9/1641; A61K 9/1652; A61K 31/4439; A61K 45/06; A61K 47/38; A61K 2300/00; C01D 5/14; C01D 7/10; C08B 3/06; C08L 1/286
See application file for complete search history.

(56) References Cited

U.S. PATENT DOCUMENTS

| | | | |
|---|---|---|---|
| 4,141,975 A | 2/1979 | Gay et al. | |
| 4,255,431 A * | 3/1981 | Junggren | ............ C07D 401/12 |
| | | | 514/338 |
| 4,447,414 A | 5/1984 | Gay et al. | |
| 5,538,989 A * | 7/1996 | Kyle | ........................ A61K 9/10 |
| | | | 514/394 |
| 5,708,017 A | 1/1998 | Dave et al. | |
| 5,731,002 A | 3/1998 | Olovson et al. | |
| 5,817,338 A | 10/1998 | Bergstrand et al. | |
| 5,824,653 A | 10/1998 | Beuvry et al. | |
| 5,840,737 A | 11/1998 | Philips | |
| 6,034,116 A | 3/2000 | Assmann et al. | |
| 6,077,541 A | 6/2000 | Chen et al. | |
| 6,136,344 A | 10/2000 | Depui et al. | |
| 6,149,942 A | 11/2000 | Scheiwe et al. | |
| 6,165,987 A | 12/2000 | Harvey | |
| 6,174,866 B1 | 1/2001 | Smoter | |
| 6,194,408 B1 | 2/2001 | Kennedy | |
| 6,316,481 B1 | 11/2001 | Freehauf | |
| 6,429,211 B1 | 8/2002 | Kennedy | |
| 6,489,346 B1 | 12/2002 | Philips | |
| 6,596,714 B1 | 7/2003 | Mihalik | |
| 6,645,988 B2 | 11/2003 | Philips | |
| 6,699,885 B2 | 3/2004 | Philips | |
| 6,733,778 B1 | 5/2004 | Chen et al. | |
| 6,737,082 B1 | 5/2004 | Picornell | |
| 6,780,882 B2 | 8/2004 | Philips | |
| 6,858,601 B2 | 2/2005 | Mihalik | |
| 7,001,889 B2 | 2/2006 | Freehauf et al. | |
| 7,396,820 B2 | 7/2008 | Cottrell et al. | |
| 7,563,773 B2 | 7/2009 | Freehauf et al. | |

(Continued)

FOREIGN PATENT DOCUMENTS

| | | |
|---|---|---|
| EP | 0114277 B1 | 2/1987 |
| EP | 0696921 B1 | 2/2001 |

(Continued)

OTHER PUBLICATIONS

Chefs Resources Scooper Sizes website, accessed Mar. 2, 2020 (Year: 2020).*
Buchanan and Andrews, Treatment and prevention of equine gastric ulcer syndrome, Jan. 2004 Veterinary Clinics of North America Equine Practice 19(3):575-97. (Year: 2004).*
Extended European Search Report, dated Mar. 19, 2020, for European Patent Application No. 17840369.7.
Hani et al., Esophagogastric ulcers in swine infected with Ascaris suum. Vet. Pathol. 16:617-618 (1979).

(Continued)

*Primary Examiner* — Kortney L. Klinkel
*Assistant Examiner* — William Y Lee
(74) *Attorney, Agent, or Firm* — K&L Gates LLP; Louis C. Cullman; Brian J. Novak (57) ABSTRACT

Described herein are pharmaceutical compositions including a proton pump inhibitor and an antiparasitic drug. In some embodiments, the compositions can be formulated as a non-solid for oral administration. The compositions can be used to treat gastrointestinal conditions. Methods of treatment using the compositions are also described.

16 Claims, 7 Drawing Sheets

(56) References Cited

U.S. PATENT DOCUMENTS

| | | | |
|---|---|---|---|
| 7,988,999 | B2 | 8/2011 | Dietrich et al. |
| 9,730,884 | B2 | 8/2017 | Marathi et al. |
| 10,137,111 | B2* | 11/2018 | Sutherland ............... A61K 9/10 |
| 10,441,575 | B2* | 10/2019 | Sutherland ............... A61P 1/04 |
| 2002/0065306 | A1 | 5/2002 | Pipers |
| 2003/0118669 | A1 | 6/2003 | Philips |
| 2003/0215527 | A1 | 11/2003 | Philips |
| 2004/0028737 | A1 | 2/2004 | Deshpande et al. |
| 2004/0037869 | A1 | 2/2004 | Cleverly et al. |
| 2004/0151759 | A1 | 8/2004 | Cleverly et al. |
| 2004/0175427 | A1 | 9/2004 | Chen et al. |
| 2005/0031700 | A1 | 2/2005 | Hall et al. |
| 2005/0032719 | A1 | 2/2005 | Cottrell et al. |
| 2005/0042282 | A1 | 2/2005 | Ieni |
| 2005/0042304 | A1 | 2/2005 | Philips |
| 2005/0054682 | A1 | 3/2005 | Philips |
| 2005/0164986 | A1 | 7/2005 | Mosher et al. |
| 2005/0249806 | A1 | 11/2005 | Proehl et al. |
| 2006/0024238 | A1 | 2/2006 | Barth et al. |
| 2006/0160783 | A1 | 7/2006 | Hickey et al. |
| 2006/0205681 | A1 | 9/2006 | Moaddeb et al. |
| 2007/0053981 | A1 | 3/2007 | Blychert et al. |
| 2007/0196496 | A1 | 8/2007 | Farber et al. |
| 2008/0020018 | A1 | 1/2008 | Moodley et al. |
| 2008/0027011 | A1 | 1/2008 | Nached et al. |
| 2008/0193531 | A1 | 8/2008 | Hermelin et al. |
| 2008/0293645 | A1 | 11/2008 | Schneider |
| 2008/0317855 | A1* | 12/2008 | Jolliffe ................. A61K 9/5015 |
| | | | 424/466 |
| 2010/0172969 | A1 | 7/2010 | Dreu et al. |
| 2010/0286154 | A1 | 11/2010 | Wieland-Berghausen et al. |
| 2010/0297220 | A1 | 11/2010 | Hall et al. |
| 2012/0046319 | A1 | 2/2012 | Mohar et al. |
| 2012/0238516 | A1 | 9/2012 | Cleverly et al. |
| 2014/0045885 | A1 | 2/2014 | Ellison |
| 2014/0154317 | A1 | 6/2014 | Al-Mehdar |
| 2014/0255503 | A1 | 9/2014 | Sangra et al. |
| 2014/0370104 | A1 | 12/2014 | Hall et al. |
| 2015/0057314 | A1 | 2/2015 | Phillips |
| 2018/0000743 | A1 | 1/2018 | Welker et al. |
| 2019/0321348 | A1* | 10/2019 | Fallin ................... A61K 47/02 |

FOREIGN PATENT DOCUMENTS

| | | | |
|---|---|---|---|
| EP | 0828480 | B1 | 8/2001 |
| EP | 0723436 | B1 | 9/2001 |
| EP | 0754061 | B1 | 6/2002 |
| EP | 1103252 | B1 | 3/2003 |
| EP | 1156806 | B1 | 4/2004 |
| EP | 1246622 | B1 | 9/2006 |
| EP | 1747776 | A1 | 1/2007 |
| EP | 1534072 | B1 | 3/2008 |
| EP | 1927354 | A1 | 6/2008 |
| EP | 0819004 | B1 | 8/2009 |
| EP | 1646404 | B1 | 1/2010 |
| EP | 2144599 | B1 | 1/2010 |
| EP | 2201952 | A1 | 6/2010 |
| EP | 2305259 | A1 | 4/2011 |
| EP | 1341524 | B1 | 10/2011 |
| EP | 2219643 | B1 | 5/2012 |
| EP | 2594258 | A1 | 5/2013 |
| EP | 2601938 | A1 | 6/2013 |
| EP | 2601947 | A1 | 6/2013 |
| EP | 1962598 | B1 | 11/2014 |
| EP | 1539116 | B1 | 2/2016 |
| WO | 1998/006407 | A1 | 2/1998 |
| WO | 2000/012064 | A1 | 3/2000 |
| WO | 2003/009846 | A1 | 2/2003 |
| WO | 2005/007117 | A2 | 1/2005 |
| WO | 2008/077130 | A2 | 6/2008 |
| WO | 2008/113803 | A1 | 9/2008 |
| WO | 2009/105568 | A1 | 8/2009 |
| WO | 2011/027333 | A1 | 3/2011 |
| WO | 2013/064535 | A1 | 5/2013 |
| WO | 2015/055974 | A1 | 4/2015 |
| WO | 2015/071668 | A1 | 5/2015 |
| WO | 2016/155786 | A1 | 10/2016 |
| WO | 2016/174052 | A1 | 11/2016 |
| WO | 2017/021992 | A1 | 2/2017 |
| WO | WO-2017021992 | A1 * | 2/2017 ........... C07D 235/28 |
| WO | 2018/031935 | A1 | 2/2018 |
| WO | 2019/113493 | A1 | 6/2019 |
| WO | 2020/093014 | A1 | 5/2020 |

OTHER PUBLICATIONS

International Search Report and Written Opinion, dated Oct. 23, 2017, for International Application No. PCT/US17/46599 filed on Aug. 11, 2017.

Chefs Resources Scooper Sizes website, accessed Mar. 2, 2020.

International Search Report and Written Opinion, dated Apr. 12, 2019, for International Application No. PCT/US18/64545 filed on Dec. 7, 2018.

International Search Report and Written Opinion, dated Jan. 24, 2020, for International Application No. PCT/US19/59545 filed on Nov. 1, 2019.

* cited by examiner

*FIG. 4A*
Grade 4 ESDG

*FIG. 4B*
Grade 0 ESDG

Grade 4 ESDG

Grade 0 ESDG

Grade 3

FIG. 6B

Grade 3

Grade 0

FIG. 6C

Grade 0

Grade 3

FIG. 7B

Grade 3

Grade 0

FIG. 7C

Grade 0

Grade 2

FIG. 8B

Grade 2

Grade 0

FIG. 8C

Grade 0

FIG. 8D

DRUG COMPOSITIONS

CROSS REFERENCE TO RELATED APPLICATIONS

This application is a continuation patent application of U.S. patent application Ser. No. 15/914,804, filed Mar. 7, 2018, which is a divisional patent application of U.S. patent application Ser. No. 15/675,435, filed Aug. 11, 2017, now U.S. Pat. No. 10,137,111, which claims the benefit of U.S. provisional patent application No. 62/373,871, filed Aug. 11, 2016, the entire disclosure of which is incorporated herein by reference.

FIELD

Described herein are compositions including combination therapy for treating gastrointestinal conditions.

SUMMARY

Described herein are pharmaceutical compositions useful for treating and/or preventing gastrointestinal conditions/discomfort in mammals. Mammals can include, but are not limited to humans, horses, camels, dogs, cats, cows, bears, rodents, sheep, goats, pigs and the like. In some embodiments, the compositions described herein can be considered veterinary compositions. In some embodiments, the compositions can include a synergistic combination of drugs and/or have an additive drug effect and can be termed combination therapy. In some embodiments, the combination therapy can include a proton pump inhibitor such as a gastric reflux drug/gastric ulcer drug and an antiparasitic drug.

The compositions can include, combined, a proton pump inhibitor and an antiparasitic drug. In one embodiment, the proton pump inhibitor is omeprazole. In another embodiment, the antiparasitic drug is fenbendazole. In some embodiments, the proton pump inhibitor is present at a concentration of about 22% w/v and/or the antiparasitic drug is present at a concentration of about 30% w/v.

Combining omeprazole with fenbendazole can provide a surprising synergistic effect that can reduce gastrointestinal recovery time and/or reduce the amount of drugs to achieve a similar or better result when compared to a single drug.

In some embodiments, the composition is formulated as a non-solid for oral administration. The non-solid can be a liquid or a paste.

The compositions can further include polyethylene glycol, sodium sulfite, carboxymethyl cellulose, and/or sodium bicarbonate.

Methods of treating a gastrointestinal ulcer are also described. The methods can comprise administering a composition including the proton pump inhibitor and the antiparasitic drug to a mammal having the gastrointestinal ulcer.

In some embodiments, the administration is performed using an oral syringe.

In some embodiments, the mammal is a human, a horse, or a camel. In some embodiments, the mammal is an athlete.

Methods of forming a composition including a proton pump inhibitor and an antiparasitic drug are also described. The methods can comprise mixing a combination including the proton pump inhibitor and the antiparasitic drug in a melted base agent to form the composition.

In some embodiments, the melted base agent is polyethylene glycol. The mixed composition can also optionally include a preservative and/or a wetting agent.

DETAILED DESCRIPTION

Described herein are pharmaceutical compositions useful for treating gastrointestinal conditions in mammals. Gastrointestinal conditions can include ulcers, reflux conditions, and the like. In some embodiments, the herein described pharmaceutical compositions can be used to treat and/or prevent an ulcer.

Mammals can include, but are not limited to, humans, horses, camels, dogs, cats, cows, bears, rodents, oxen, bison, buffalo, caribou, moose, deer, elk, sheep, goats, pigs, rabbits, pouched mammals, primates, carnivores, and the like.

In some embodiments, the mammals can be athletes. Athletes can include, but are not limited to, race horses, race camels, race dogs, racing humans, jumping horses, jumping camels, jumping dogs, jumping humans, dancing horses, dancing camels, dancing dogs, dancing humans, and the like. In other embodiments, the mammals can be working mammals. Working mammals can include, but are not limited to, mammals that exert physical energy for a purpose. That purpose can be pulling a load, pushing a load, carrying a load, carrying a human, jumping, dancing, climbing, swimming, and the like.

In some embodiments, the mammal is a thoroughbred horse. Thoroughbreds can include, but are not limited to Arabians, Standardbreds, Quarter Horses, and the like.

Prior to discovery of the present compositions, treatment of gastrointestinal conditions, such as an ulcer, took at least four weeks to mitigate, reduce, or diminish the condition. In some cases, treatment could take as long as a year. In other cases, treatment would be ongoing indefinitely. In some cases, the longer a mammal is subjected to treatment with particular drugs, the more side effects the mammal may be subjected to.

The present combinations can produce synergistic and/or additive effects in reducing a symptom associated with a gastrointestinal condition. Consequently, a considerably reduced dose of therapeutic compounds can be given for an equivalent effect for each individual therapeutic compound or an equivalent amount of each therapeutic compound can be given to achieve a larger and/or more rapid response. In some embodiments, the compositions can reduce side-effects and drug burden.

As used herein, the term "pharmaceutical composition" refers to a therapeutically effective concentration of the drugs and other ingredients described herein. As used herein, the term "pharmaceutically acceptable" refers to compositions that do not produce an adverse, allergic, or other untoward or unwanted reaction when administered to a mammal.

The drug combination or combination therapy disclosed herein can be formulated in any appropriate form. An appropriate from can be a form that is easy to administer, allows the stability of active agent(s), allows the introduction of active agent(s), and the like. Appropriate forms can include powders, semi-solids, liquids, pastes, suspensions, inhalable dry powders, inhalable formulations, solids, granules, combinations thereof, and the like.

The drug combination or combination therapy disclosed herein may be made into a semi-solid formulation. Semi-solid formulations can be made for enteral or topical administration. Semi-solid formulations suitable for enteral administration include, without limitation, pastes, and gels. Semi-solid formulations suitable for topical or oral administration include, without limitation, ointments, creams, salves, pastes, and gels. The drug combination or combination therapy disclosed herein intended for such administration may be prepared according to any method known in the art for the manufacture of pharmaceutical compositions.

The drug combination or combination therapy may be made into a liquid formulation. Liquid formulations suitable for enteral or parenteral administration include, without limitation, solutions, syrups, elixirs, dispersions, emulsions, and suspensions. The drug combination or combination therapy disclosed herein intended for such administration may be prepared according to any method known in the art for the manufacture of pharmaceutical compositions. In such liquid dosage forms, the drug combination disclosed herein may be admixed with (a) suitable aqueous and non-aqueous carriers, (b) diluents, (c) solvents, such as, e.g., water, ethanol, propylene glycol, polyethyleneglycol, glycerol, vegetable oils, such as, e.g., rapeseed oil and olive oil, and injectable organic esters such as ethyl oleate; and/or fluidity agents, such as, e.g., surfactants or coating agents like lecithin. In the case of dispersions and suspensions, fluidity can also be controlled by maintaining a particular particle size.

Liquid and/or semi-solid formulations may be formulated with sweetening agents, for example glycerol, propylene glycol, sorbitol or sucrose. Such formulations may also contain one or more demulcent, preservative, flavoring agent, and/or coloring agent.

Liquid and/or semi-solid suspensions may be formulated by suspending the drug combination in an admixture with suitable excipients. Suitable excipients can be suspending agents, such as sodium carboxymethyl cellulose, methylcellulose, hydroxypropylmethylcellulose, sodium alginate, pectin, polyvinyl pyrrolidone, polyvinyl alcohol, natural gum, agar, gum tragacanth, and/or gum acacia.

Oily suspensions may be formulated by suspending the drug combination in an admixture with (a) vegetable oils including almond oil, arachis oil, avocado oil, canola oil, castor oil, coconut oil, corn oil, cottonseed oil, grape seed oil, hazelnut oil, hemp oil, linseed oil, olive oil, palm oil, peanut oil, rapeseed oil, rice bran oil, safflower oil, sesame oil, soybean oil, soya oil, sunflower oil, walnut oil, wheat germ oil, or a combination thereof, (b) a saturated fatty acid, an unsaturated fatty acid, or a combination thereof, such as palmitic acid, stearic acid, oleic acid, linoleic acid, linolenic acid, or a combination thereof, (c) mineral oil such as liquid paraffin, (d) surfactants or detergents. The oily suspensions may contain a thickening agent such as beeswax, hard paraffin, or cetyl alcohol.

In some embodiments, oils can be used as a carrier or in the place of a carrier such as polyethylene glycol. The drug combination disclosed herein may be made into an inhaled formulation. Inhaled formulations suitable for enteral or parenteral administration include, without limitation, aerosols and/or dry powders. The drug combination disclosed herein intended for such administration may be prepared according to any method known in the art for the inhalable manufacture of pharmaceutical compositions.

The drug combination may be made into a solid formulation. Solid formulations suitable for enteral or parenteral administration include, without limitation, capsules, tablets, pills, troches, lozenges, powders and granules suitable for inhalation, ingestion, or for reconstitution into sterile injectable solutions or dispersions. In other embodiments, the drug combination can be in a semi-solid form such as a paste. The drug combination intended for such administration may be prepared according to any method known to the art for the manufacture of pharmaceutical compositions. In such solid dosage forms, the drug combination may be admixed with (a) at least one inert customary excipient (or carrier), such as, e.g., sodium citrate or dicalcium phosphate or (b) fillers or extenders, such as for example, starch, lactose, sucrose, glucose, mannitol, isomalt, and silicic acid, (c) binders, such as, e.g., carboxymethylcellulose, alignates, gelatin, polyvinylpyrrolidone, sucrose and acacia, (d) humectants, such as, e.g., glycerol, (e) disintegrating agents, such as, e.g., agar-agar, calcium carbonate, corn starch, potato starch, tapioca starch, alginic acid, certain complex silicates and sodium carbonate, (f) solution retarders, such as, e.g., paraffin, (g) absorption accelerators, such as, e.g., quaternary ammonium compounds, (h) wetting agents, such as, e.g., cetyl alcohol and glycerol monostearate, (i) adsorbents, such as, e.g., kaolin and bentonite, (j) lubricants, such as, e.g., talc, stearic acid, calcium stearate, magnesium stearate, solid polyethylene glycols, sodium lauryl sulfate or mixtures thereof, and (k) buffering agents. The tablets may be uncoated or they may be coated by known techniques to delay disintegration and absorption in the gastrointestinal tract and thereby provide a sustained action over a longer period.

In some embodiments, the compositions can include a proton pump inhibitor such as a gastric reflux drug/gastric ulcer drug in combination with an antiparasitic drug. In some embodiments, the antiparasitic drug can be included in the composition at most about 35% (w/v), at most about 40% (w/v), about 15% (w/v), about 20% (w/v), about 25% (w/v), about 30% (w/v), about 35% (w/v), about 40% (w/v), about 45% (w/v), about 50% (w/v), between about 20% and about 40% (w/v), or between about 25% and about 35% (w/v). In some embodiments, the gastric reflux drug/gastric ulcer drug can be included in the composition at most about 30% (w/v), at most about 25% (w/v), about 10% (w/v), about 15% (w/v), about 20% (w/v), about 21% (w/v), about 22% (w/v), about 23% (w/v), about 25% (w/v), about 30%

(w/v), about 35% (w/v), about 40% (w/v), between about 20% and about 25% (w/v), or between about 15% and about 30% (w/v).

In one embodiment, the gastric reflux drug/gastric ulcer drug is omeprazole. In one embodiment, the antiparasitic drug is fenbendazole.

Combining omeprazole with fenbendazole can provide a surprising synergistic effect that can reduce gastric ulcer recovery time. In other embodiments, combining omeprazole with fenbendazole can provide a surprising synergistic effect that can reduce recovery time for other gastrointestinal conditions.

A composition disclosed herein may optionally include a pharmaceutically-acceptable carrier that facilitates processing of a drug into pharmaceutically-acceptable compositions. Such a carrier can be mixed with a drug or drugs or permitted to dilute or enclose the drug or drugs and can be a solid, semi-solid, or liquid agent. It is understood that the drug or drugs can be soluble or can be delivered as a suspension in the desired carrier or diluent. In some embodiments, the drugs can be formulated as a paste. Any of a variety of pharmaceutically acceptable carriers can be used including, without limitation, aqueous media such as, e.g., water, saline, glycine, hyaluronic acid and the like; solid carriers such as, e.g., polyethylene glycol, polyethylene oxide, mannitol, lactose, starch, magnesium stearate, sodium saccharin, talcum, cellulose, glucose, sucrose, magnesium carbonate, and the like; solvents; dispersion media; coatings; isotonic and absorption delaying agents; or any other inactive ingredient. Selection of a pharmacologically acceptable carrier can depend on the mode of administration. In some embodiments, solid carriers can be melted.

In one embodiment, the pharmaceutically-acceptable carrier is a base agent melted to form a paste. In some embodiments, each base agent can be included in the composition at most about 10% (w/v), at most about 6% (w/v), about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), between about 1% and about 10% (w/v), or between about 5% and about 7% (w/v).

In one embodiment, the base agent can be a polyethylene glycol. Polyethylene glycol used as a base agent can have a molecular weight of greater than about 1,000 g/mol, greater than about 1,200 g/mol, greater than about 1,400 g/mol, between about 1,000 g/mol and about 1,600 g/mol, between about 1,300 g/mol and about 1,500 g/mol, or between about 1,400 g/mol and about 1,500 g/mol. In one embodiment, the polyethylene glycol has a molecular weight of about 1,450 g/mol.

A pharmaceutical composition disclosed herein can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, flavoring agents, coloring agents, suspension agents, and the like.

Various buffers and means for adjusting pH can be used to prepare a pharmaceutical composition disclosed herein. Such buffers include, without limitation, acetate buffers, citrate buffers, phosphate buffers, neutral buffered saline, phosphate buffered saline, bicarbonate buffers, and borate buffers. It is understood that acids or bases can be used to adjust the pH of a composition as needed. Bases can include sodium hydroxide. In one embodiment, sodium bicarbonate is used as a buffer. In another embodiment, sodium hydroxide is used to make the composition more alkaline. In some embodiments, the alkalinity of the composition can be a pH greater than about 7, greater than about 7.5, greater than about 8, greater than about 8.5, greater than about 9, greater than about 9.5, or greater than about 10.

In some embodiments, a buffer(s) can be included in the composition at most about 10% (w/v), at most about 5% (w/v), about 1% (w/v), about 2% (w/v), about 3% (w/v), about 4% (w/v), about 5% (w/v), about 6% (w/v), about 7% (w/v), about 8% (w/v), about 9% (w/v), about 10% (w/v), between about 1% and about 10% (w/v), or between about 4% and about 6% (w/v).

Pharmaceutically acceptable antioxidants can include, without limitation, sodium metabisulfite, sodium thiosulfate, acetylcysteine, butylated hydroxyanisole and butylated hydroxytoluene.

Flavoring agents can provide a composition that smells good and/or tastes good. Non-human mammals may need encouragement to consume the compositions described. Thus, flavoring agents may be added that stimulate appeal to or that naturally attract a particular mammal species. Flavoring agents can make orally administrable compositions taste like apple, orange, lemon, grape, butterscotch, cherry, blueberry, raspberry, strawberry, honey, peppermint, spearmint, cinnamon, peach, watermelon, chocolate, espresso, mango, banana, carrot, cantaloupe, guava, acai, cheese, tomato, caramel, taffy, lime, and the like. Flavor combinations can also be provided.

Preservatives can include, without limitation, sodium sulfite, sodium sulfide, benzalkonium chloride, chlorobutanol, thimerosal, phenylmercuric acetate, phenylmercuric nitrate, a stabilized oxy chloro composition and chelants, such as, e.g., DTPA (diethylenetriaminepentaacetic acid) or DTPA-bisamide, calcium DTPA, and CaNaDTPA-bisamide. In one embodiment, sodium sulfite is used as a preservative.

In some embodiments, a preservative(s) can be included in the composition at most about 0.2% (w/v), at most about 0.5% (w/v), about 0.05% (w/v), about 0.06% (w/v), about 0.07% (w/v), about 0.08% (w/v), about 0.09% (w/v), about 0.1% (w/v), about 0.11% (w/v), about 0.12% (w/v), about 0.13% (w/v), about 0.14% (w/v), about 0.15% (w/v), between about 0.05% and about 0.15% (w/v), or between about 0.09% and about 0.11% (w/v).

Tonicity adjustors can include, without limitation, salts such as, e.g., sodium chloride, potassium chloride, mannitol or glycerin and other pharmaceutically acceptable tonicity adjustors.

Suspension agents can include, without limitation, carboxymethyl cellulose. The suspension agent can be used to keep the drug(s) dispersed evenly in the composition.

In some embodiments, the suspension agent(s) can be included in the composition at most about 0.2% (w/v), at most about 0.5% (w/v), about 0.05% (w/v), about 0.1% (w/v), about 0.2% (w/v), about 0.3% (w/v), about 0.4% (w/v), about 0.5% (w/v), about 0.8% (w/v), about 1% (w/v), between about 0.1% and about 0.3% (w/v), or between about 0.1% and about 1% (w/v).

Wetting agents can include, without limitation, polyethylene glycol. In some embodiments, the polyethylene glycol can be a low molecular weight polyethylene glycol. The low molecular weight polyethylene glycol can have a molecular weight of less than about 500 g/mol, less than about 300 g/mol, greater than about 100 g/mol, between about 200 g/mol and about 400 g/mol, between about 100 g/mol and about 500 g/mol, or between about 250 g/mol and about 350 g/mol. In one embodiment, the polyethylene glycol has a molecular weight of about 300 g/mol.

In some embodiments, the wetting agent can be included in the composition at least about 35% (w/v), at least about 60% (w/v), about 35% (w/v), about 40% (w/v), about 50% (w/v), about 60% (w/v), about 65% (w/v), about 70% (w/v), between about 35% and about 40% (w/v), or between about 60% and about 70% (w/v).

In one embodiment, a composition can include drugs formulated as a paste including carboxymethyl cellulose, sodium sulfite, sodium bicarbonate, and polyethylene glycol. In some embodiments, a composition can include drugs formulated as a liquid including carboxymethyl cellulose, sodium sulfite, sodium bicarbonate, and polyethylene glycol. In one embodiment, a composition can include omeprazole, fenbendazole, carboxymethyl cellulose, sodium sulfite, sodium bicarbonate, and polyethylene glycol in solution.

In some embodiments, a composition can be provided as granules. In some embodiments, the granules can be provided as a scoop. A scoop can be provided as a 30 Scoop, a 60 Scoop, or a 100 Scoop size.

In some embodiments, a composition can be provided as a suspension. A suspension can be provided as a 480 mL aliquot, a 960 mL aliquot, or a 3,785 mL aliquot.

In one embodiment, a composition or combination therapy can include about 2.2 g omeprazole, about 3 g fenbendazole, about 0.02 g carboxymethyl cellulose, 0.01 g sodium sulfite, 0.5 mL sodium bicarbonate, and about 1.2 g polyethylene glycol in 10 mL of solution. In some embodiments, the formulation is maintained at a pH greater than 8.

In some embodiments, a composition can be provided as a 10 mL oral paste including 2.2 g of omeprazole and 3 g of fenbendazole. The composition can be stored at a temperature between about 20° C. and about 25° C.

In some embodiments, the composition can be provided in a dial-a-dose oral syringe. In one embodiment, the dial-a-dose syringe is a 30 mL syringe.

In some embodiments, the compositions can include inactive ingredients such as, but not limited to, carboxymethylcellulose, sodium bicarbonate, sodium sulfite, polyethyleneglycol, distilled water, and optionally sodium hydroxide. In other embodiments, each 1 mL of composition can include inactive ingredients such as, but not limited to, 2 mg of carboxymethylcellulose, 3.8 mg of sodium bicarbonate, 1 mg of sodium sulfite, 60 mg of polyethyleneglycol 1450, 536 mg of polyethyleneglycol 3, distilled water, and optionally sodium hydroxide to adjust pH.

The drug combination or combination therapy disclosed herein may be formulated for either local or systemic delivery using topical, enteral, or parenteral routes of administration.

In some embodiments, the compositions described herein are delivered orally. When delivered orally, the compositions can be administered using an oral medication syringe.

The compositions described herein can be administered at amounts of about 10 cc, about 15 cc, about 20 cc, about 25 cc, about 30 cc, about 35 cc, about 40 cc, about 45 cc, about 50 cc, about 55 cc, about 60 cc, about 65 cc, about 70 cc, about 75 cc, about 80 cc, about 85 cc, about 90 cc, about 95 cc, about 100 cc, at least about 10 cc, at least about 20 cc, between about 20 cc and about 50 cc, between about 20 cc and about 30 cc, between about 25 cc and about 35 cc, between about 30 cc and about 35 cc, or between about 25 cc and about 30 cc per administration.

Administration can be any interval that results in a therapeutic response. In some embodiments, administration can be one, two, three, four, five, or more times per day. In other embodiments, administration can be every other day, every third day, every fourth day, every fifth day, every sixth day, once per week, twice per month, monthly, and the like. In one embodiment, administration is once per day. In still other embodiments, administration can be for the remaining life of the mammal.

In some embodiments, when the animal is an athlete, administration can be before an athletic event such, as for example, but not limited to every day, every other day, every third day, every fourth day, every fifth day, every sixth day, once per week, twice per month, and the like leading up to the athletic event.

In other embodiments, when the animal is an athlete, administration can be after an athletic event such as, for example, but not limited to every day, every other day, every third day, every fourth day, every fifth day, every sixth day, once per week, twice per month, and the like after the athletic event.

In some embodiments, administration can include both before and after an athletic event. In some embodiments, the administration is the same before and after an athletic event. In other embodiments, the administration is different before and after the athletic event.

Methods of forming administrable compositions are also described. Methods can include first weighing the ingredients for the composition. Then, the polyethylene glycol base agent is heated until it melts. To the melted base agent, omeprazole, carboxymethyl cellulose, sodium sulfite, and fenbendazole are added. The contents are then mixed until a smooth paste is achieved. The paste is wetted as necessary with a polyethylene glycol wetting agent. The pH is checked and adjusted as necessary using sodium hydroxide (e.g., pellets). In some embodiments, the pH is adjusted to an alkaline pH. In some embodiments, the alkaline pH is greater than about 8. The resulting paste is then pulled into a syringe for storage, sterilization, administration, or the like.

Some embodiments provide a kit including an oral syringe pre-filled with a composition described herein and instruction for use in a unifying container.

Other embodiments provide a kit including a vial or other appropriate container containing a composition described herein and instruction for use in a unifying container.

Still other embodiments provide a kit including a vial or other appropriate container containing a composition described herein, a syringe, and instruction for use in a unifying container.

Some embodiments provide a kit including seven oral syringes pre-filled with a composition described herein and instruction for a week's use in a unifying container.

Other embodiments provide a kit including a vial or other appropriate container containing a composition described herein for seven days of use and instruction for use in a unifying container.

Still other embodiments provide a kit including a vial or other appropriate container containing a composition described herein for seven days of use, seven oral syringes, and instruction for use in a unifying container.

Once housed in a delivery device or included in a kit, the composition/delivery devices/kits can be sterilized using conventional sterilization techniques without substantial degradation to the composition. Without substantial degradation to the composition means that the composition retains greater than 80%, greater than 90%, greater than 95%, or greater than 99% of its activity. In some embodiments, the compositions remain unaffected by sterilization. Sterilization can be by at least one sterilization technique including, but not limited to, gamma irradiation, pressure sterilization, and/or steam sterilization.

In some embodiments, the compositions described herein can retain substantially all potency for at least 14 days. In some embodiments, the compositions described herein can retain substantially all potency for at least 30 days. In some embodiments, the compositions described herein can retain substantially all potency for at least 60 days. In some embodiments, the compositions described herein can retain substantially all potency for at least 90 days. In some embodiments, the compositions described herein can retain substantially all potency for at least 180 days. In some embodiments, the compositions described herein can retain substantially all potency for at least 360 days. In some embodiments, the compositions described herein can retain substantially all potency for longer than 360 days.

Substantially all potency means that the compositions retain at least greater than 80%, greater than 90%, greater than 95%, or greater than 99% of its activity when stored at appropriate conditions. In some embodiments, appropriate conditions can be at room temperature. In some embodiments, appropriate conditions can be without direct light. In some embodiments, appropriate conditions can be under refrigeration or refrigerated.

The compositions described herein can reduce incidence time of a gastrointestinal condition. In one embodiment, the compositions described herein can reduce the incidence time of a gastric ulcer. In some embodiments, the compositions can simply treat an ulcer. Treatment using omeprazole alone is generally prescribed for once daily administration for four weeks. Many times, omeprazole is prescribed for an additional four week period to fully treat a gastrointestinal condition. In some instances, omeprazole can be administered to some mammals indefinitely to treat ongoing gastrointestinal conditions. In these mammals, omeprazole alone may not fully treat the gastrointestinal condition, even after eight weeks of treatment.

In some embodiments, the herein described compositions can reduce the incidence time of a gastrointestinal condition when compared to treatment with omeprazole alone by at least about 10%, by at least about 20%, by at least about 50%, by at least about 75%, by at least about 100%, by at least about 150%, by at least about 200%. In some embodiments, treatment time can be reduced by at least 1 week, at least 2 weeks, at least 3 weeks, at least 4 weeks, at least 5 weeks, or at least 6 weeks. In some embodiments, the herein described compositions can fully treat a gastrointestinal condition thereby not requiring indefinite treatment.

As a result of the reduced incidence time, a composition disclosed herein may reduce an unwanted side effect elicited by administration of omeprazole and/or fenbendazole. In one embodiment, unwanted side effects of omeprazole include, without limitation, anorexia, colic, nausea, vomiting, flatulence, diarrhea, hematologic abnormalities, urinary tract infections, proteinuria, and/or central nervous system disturbances. In one embodiment, unwanted side effects of fenbendazole include, without limitation, vomiting, drooling, and/or diarrhea.

Further, as a result of the synergistic and/or additive effects of the herein described compositions, a reduced load of drugs may be required to achieve similar results to the drugs alone. In some embodiments, treatment using the described compositions may only require about 10%, about 20%, about 30%, about 40%, about 50%, about 60%, about 70%, or about 80% of a general dose of omeprazole. In other embodiments, treatment using the described compositions may only require about 10%, about 20%, about 30%, about 40%, about 50%, about 60%, about 70%, or about 80% of a general dose of fenbendazole.

In some embodiments, compositions described herein can be administered regularly to aid in preventing an ulcer or other gastrointestinal issue. The compositions can be administered daily after treatment of an ulcer to prevent recurrence of the ulcer. In other embodiments, the compositions can be administered before evidence of an ulcer exists to prevent an ulcer from ever occurring. In some embodiments, the herein described compositions can be administered for an entire lifetime to prevent the occurrence of ulcers.

In some embodiments, horses can be clinically healed within about 30 days of treatment. In other embodiments, horses can be clinically healed in less than about 30 days of treatment. In other embodiments, greater than about 80% of horses can be clinically healed within about 30 days of treatment. In other embodiments, greater than about 80% of horses can be clinically healed in less than about 30 days of treatment. In other embodiments, about 80% of horses can be clinically healed after 28 days of treatment. In some embodiments, clinically healed can mean that a horse has an ulcer score of Grade 0 or Grade 1. In other embodiments, clinically healed can mean that a horse has an ulcer score of Grade 0.

In other embodiments, about 90% of horses can be clinically healed after 30 days of treatment. In other embodiments, greater than about 90% of horses can be clinically healed within about 30 days of treatment. In other embodiments, greater than about 90% of horses can be clinically healed in less than about 30 days of treatment. In other embodiments, about 90% of horses can be clinically healed after 30 days of treatment.

In other embodiments, about 95% of horses can be clinically healed after 30 days of treatment. In other embodiments, greater than about 95% of horses can be clinically healed within about 30 days of treatment. In other embodiments, greater than about 95% of horses can be clinically healed in less than about 30 days of treatment. In other embodiments, about 95% of horses can be clinically healed after 30 days of treatment.

In some embodiments, horses can be clinically healed within about 15 days of treatment. In other embodiments, horses can be clinically healed in less than about 15 days of treatment. In other embodiments, greater than about 80% of horses can be clinically healed within about 15 days of treatment. In other embodiments, greater than about 80% of horses can be clinically healed in less than about 15 days of treatment. In other embodiments, about 80% of horses can be clinically healed after 14 days of treatment.

In some embodiments, horses can be clinically healed within about 14 days of treatment. In other embodiments, horses can be clinically healed in less than about 14 days of treatment. In other embodiments, greater than about 80% of horses can be clinically healed within about 14 days of treatment. In other embodiments, greater than about 80% of horses can be clinically healed in less than about 14 days of treatment.

In other embodiments, about 90% of horses can be clinically healed after 14 days of treatment. In other embodiments, greater than about 90% of horses can be clinically healed within about 14 days of treatment. In other embodiments, greater than about 90% of horses can be clinically healed in less than about 14 days of treatment. In other embodiments, about 90% of horses can be clinically healed after 14 days of treatment.

In other embodiments, about 95% of horses can be clinically healed after 14 days of treatment. In other embodiments, greater than about 95% of horses can be clinically healed within about 14 days of treatment. In other embodiments, greater than about 95% of horses can be clinically healed in less than about 14 days of treatment. In other embodiments, about 95% of horses can be clinically healed after 14 days of treatment.

In some embodiments, the herein described compositions can be administered without the need for rest or reduced training. In an embodiment of treatment of a race horse, the compositions can be administered during training. In some embodiments, the training can be heavy training in preparation for a race.

In other embodiments, treatment with the herein described compositions can enhance a patient's ability to perform at an optimal level. In some embodiments, prior treatments require a patient to be treated for months, years, or even a lifetime. Unlike the herein described compositions where a patient can train during treatment, prior treatments can prevent training or optimal performance.

In some embodiments, prior treatments require a patient to be treated for months, years, or even a lifetime. Unlike the herein described compositions where a patient can train during treatment, prior treatments can prevent training or optimal performance.

In some embodiments, when administered to a racing horse or camel, treatment with the herein described compositions can enhance the animals performance when compared to being treated using any prior method and/or composition. In some embodiments, the herein described compositions can allow a treated horse or camel to perform at an optimal level within the periods described herein, whereas a horse or camel treated by any prior composition or method can only perform at a diminished level and may never again achieve optimal performance levels. Thus, in some embodiments, the herein described compositions and methods can increase the running performance of a horse or camel when compared to prior treatment compositions and methods.

In one embodiment, described is a method for increasing a mammal's athletic performance, the method including treating a horse's ulcer using a composition as described herein.

In one embodiment, described is a method for increasing a horse's athletic performance, the method including treating a horse's ulcer using a composition as described herein.

In one embodiment, described is a method for increasing a camel's athletic performance, the method including treating a horse's ulcer using a composition as described herein.

In one embodiment, described is a method for increasing a human's athletic performance, the method including treating a horse's ulcer using a composition as described herein.

In some embodiments, treatment using the herein described compositions can transform an unfit horse into a winning race horse.

Ulcers described herein are graded on a scale of 0 to 4, 4 being most severe and 0 being clinically healed. In some embodiments, a grade of 1 can also be considered clinically healed. In some embodiments, a score of >1 indicates that a horse has an ulcer(s). A score of <1 but >0 may indicate that a horse has a healing ulcer despite not exhibiting an active ulcer.

Example 1

Horse Treatment

Figure 1:
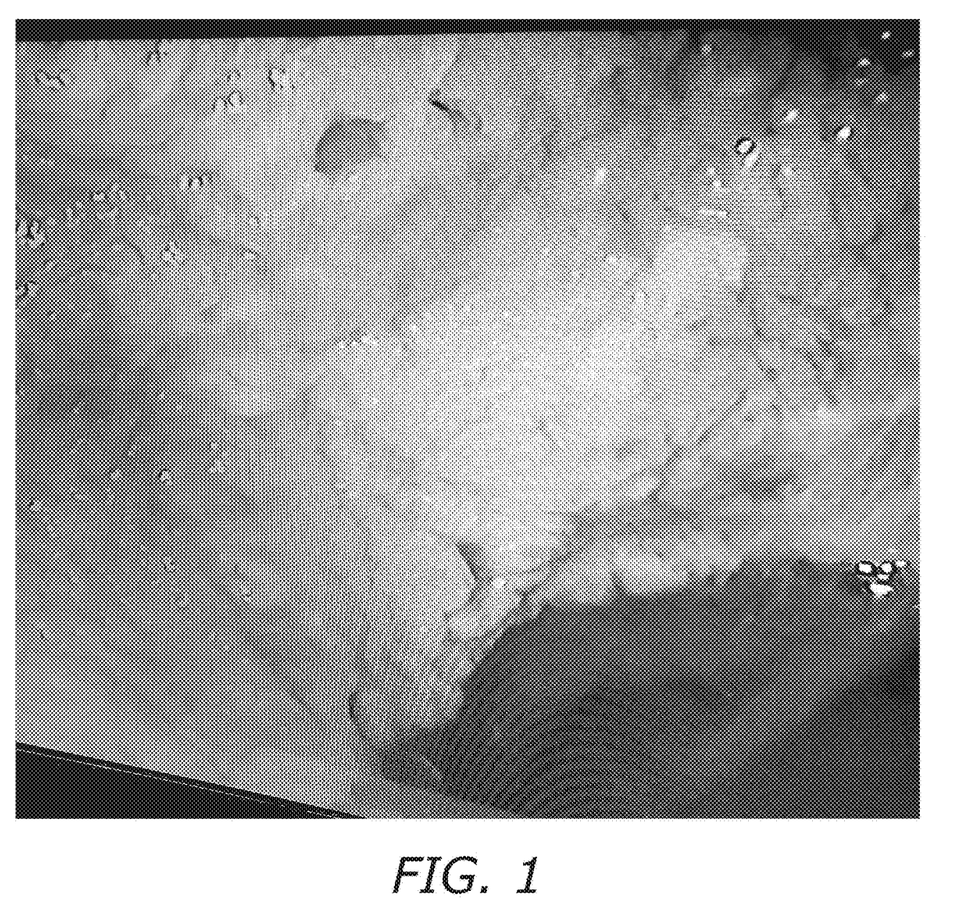
FIG. 1 illustrates a horse's stomach lining. Dark pitting and rough edges on the horse's stomach lining can be seen. The horse had a Grade 2 ulcer and was being treated ineffectively with a commercially available drug.
Figure 2:
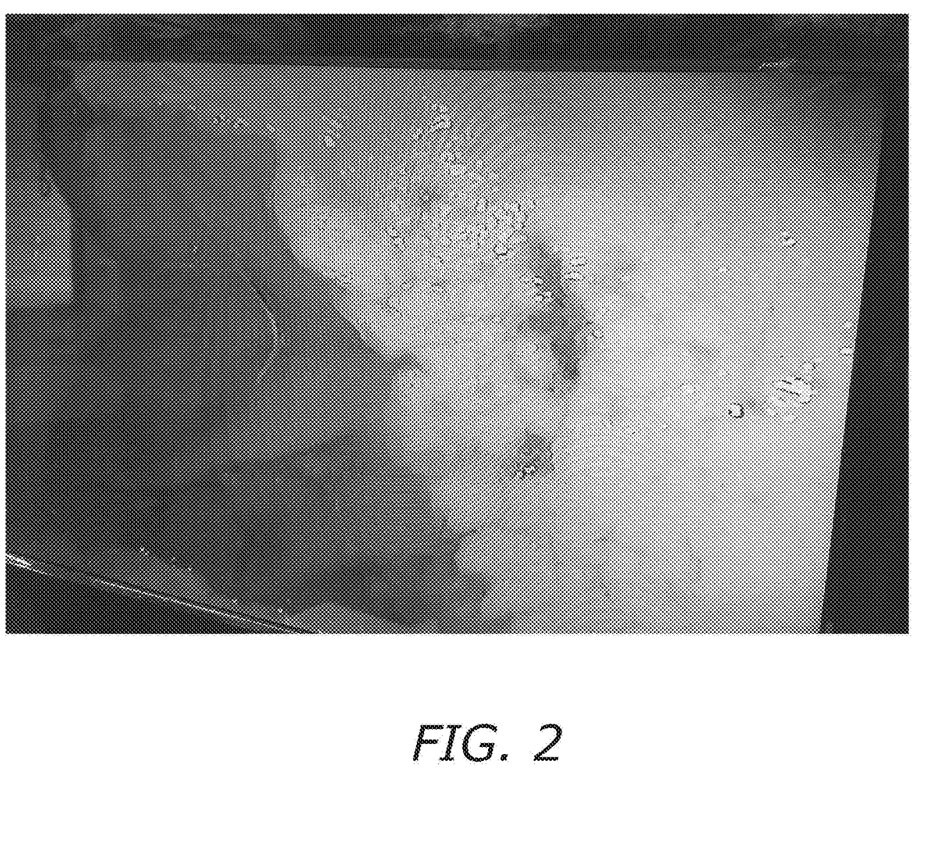
FIG. 2 illustrates another horse's stomach lining. Dark pitting and rough edges on the lining of this horse's stomach can be seen. The horse had a Grade 2 ulcer and was being treated ineffectively with the same commercially available drug.

Two horses were treated with a composition including 22% w/v omeprazole and 30% w/v fenbendazole. The horses were started on the composition while already taking GASTROGUARD® (37% w/w omeprazole, Bio-Botanica, Inc., New York) at a dose of half a tube per day. A dose of GASTROGUARD® is generally 4 mg/kg of horse weight. GASTROGUARD® is a paste for horses that contains 37% w/w omeprazole. Horses were not responding to the GASTROGUARD® treatment. The horses both presented Grade 2 ulcers which are characterized by the dark pitting and rough edges of the stomach lining illustrated in FIGS. 1-2. The horses had major discomfort.

Figure 3:
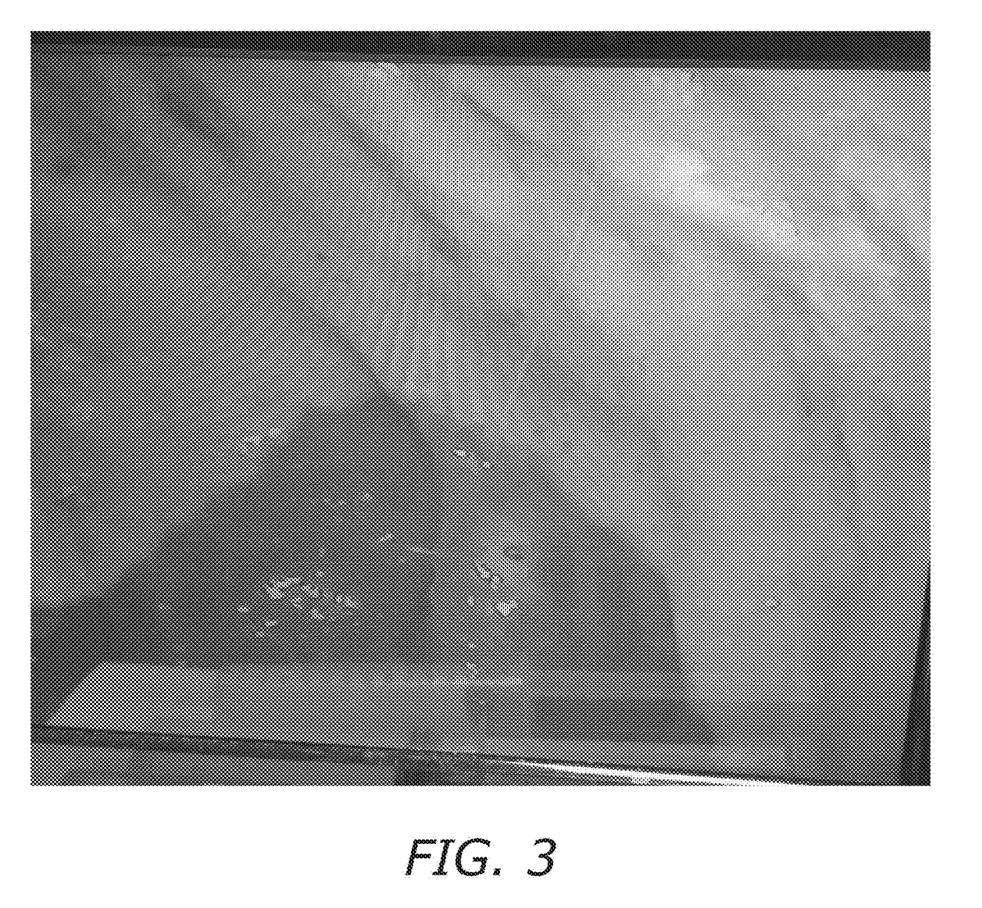
FIG. 3 illustrates the horse's stomach from FIG. 2 17 days after beginning treatment with the present compositions. The stomach lining after 17 days is now smooth and has no more dark pitting.

After just 17 days of treatment using the composition including 22% w/v omeprazole and 30% w/v fenbendazole, each horse was graded normal. This normal grade stomach is illustrated in FIG. 3. FIG. 3 illustrates that the stomach lining is now smooth and no dark spots exist.

Example 2

Horse Treatment

Figure 4A:
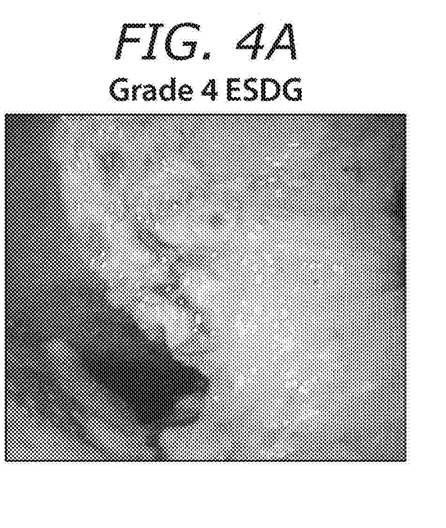
FIG. 4A is a Grade 4 ESDG in a three year old thoroughbred filly (TB filly) before treatment and FIG. 4B is a Grade 0 ESDG in the same three year old TB filly after treatment.
Figure 4B:
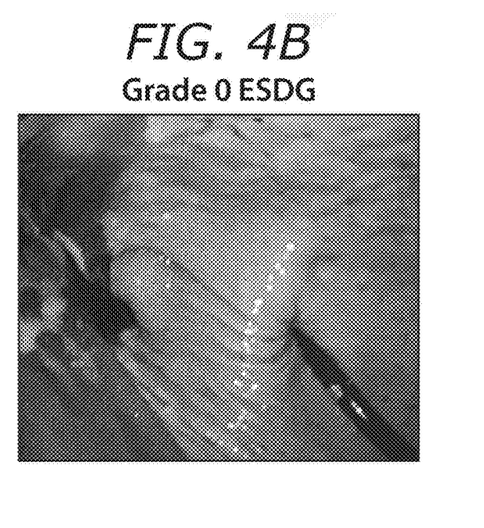

Two horses were treated with a composition including 22% w/v omeprazole and 30% w/v fenbendazole. One horse was a three year old TB Filly that had a Grade 4 ESDG. FIG. 4A illustrates the severity of the ulcer. After 14 days of treatment, the horse presented a Grade 0 ESDG as illustrated in FIG. 4B.

Figure 5A:
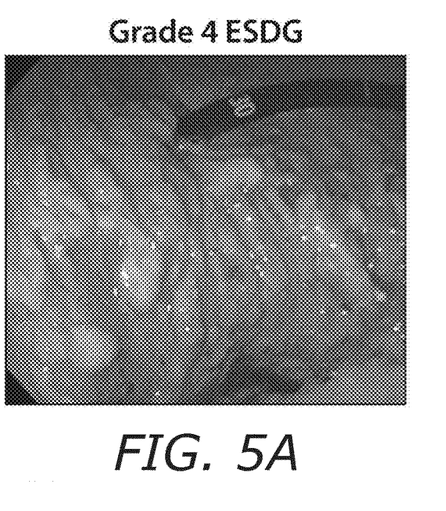
FIG. 5A is a Grade 4 ESDG in a four year old TB filly before treatment and FIG. 5B is a Grade 0 ESDG in the same four year old TB filly after treatment.
Figure 5B:
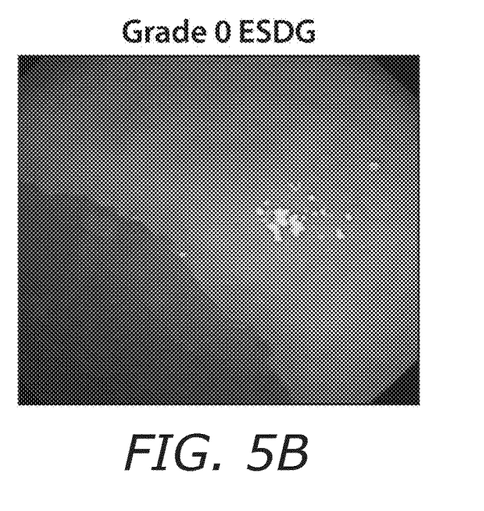

Another horse was a four year old TB Filly that had a Grade 4 ESDG. FIG. 5A illustrates the severity of the ulcer. After 28 days of treatment, the horse presented a Grade 0 ESDG as illustrated in FIG. 5B.

Example 3

Camel Treatment

A camel is treated with a composition including omeprazole and fenbendazole. The camel presented a Grade 2 ulcer which is characterized by the dark pitting and rough edges of the stomach lining. The camel has major discomfort. After just 14 days of treatment using the composition including omeprazole and fenbendazole, the camel presented a stomach that is graded as normal.

Example 4

Horse Ulcer Prevention

A horse is administered a composition once daily including 22% w/v omeprazole and 30% w/v fenbendazole. The horse presents no signs of an ulcer. The horse never develops an ulcer.

Example 5

Horse Ulcer Prevention

A horse is administered a composition twice daily including 22% w/v omeprazole and 30% w/v fenbendazole. The horse presents no signs of an ulcer. The horse never develops an ulcer.

Example 6

Horse Ulcer Reoccurrence Prevention

A horse is administered daily a composition including 22% w/v omeprazole and 30% w/v fenbendazole after being treated for an ulcer. At the initiation of treatment, the horse presents no signs of an ulcer. The horse does not develop a reoccurrence of the ulcer during the year of treatment.

Example 7

Scoop Preparation

A scoop is prepared that includes 2.2 g of omeprazole USP powder 99.47, 3 g of fenbendazole EP powder 100.5, 0.852 g green apple flavor #6005 (sugar free), and 16.52 g of dextrose USP anhydrous powder. The contents are weighed and mixed together one at a time: omeprazole, fenbendazole, apple flavor, and dextrose. The powders are blended until an even color and smooth mixture (free of clumps) is obtained throughout the mixture. Then 677.16 g of the mixture is dispensed into 32 oz. jars with a 30 cc scoop.

Example 8

Suspension Preparation

A suspension is prepared that includes 140.8 g of omeprazole USP powder 99.47, 28.8 mL aqueous green apple flavor (sugar free), 0.96 g of sodium sulfite FCC powder 99.14, 96 mL of sodium bicarbonate, 3.36 g of carboxymethylcellulose NA (medium), 192 g of fenbendazole EP powder 100.5, and 960 mL of polyethylene glycol 300 NF liquid. The contents are weighed and mixed together one at a time: omeprazole, sodium sulfite, carboxymethylcellulose, apple flavor, and ranitidine. To an appropriate sized beaker is added 50% total volume of the polyethylene glycol. Then, omeprazole, sodium sulfite, apple flavor, and ranitidine are added and then blended. Sodium bicarbonate is added to the mixture and mixed/blended until uniform. Carboxymethylcellulose is added to the mixture and mixed/blended until uniform. The pH is checked and adjusted to pH level 9-10.5 using NaOH or HCl.

Example 9

Horse Treatment

Figure 6A:
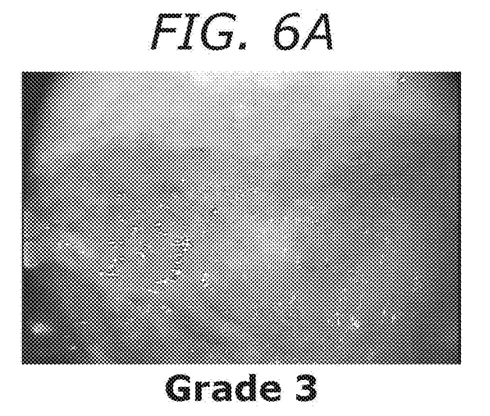
FIGS. 6A and 6B illustrate an ESDG in a horse before treatment and FIGS. 6C and 6D illustrate a Grade 0 ESDG in the same horse after treatment.
Figure 6B:
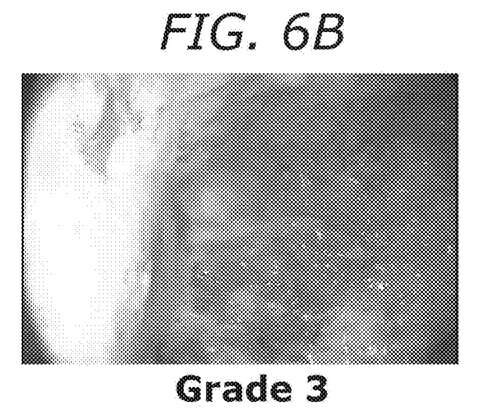
Figure 6C:
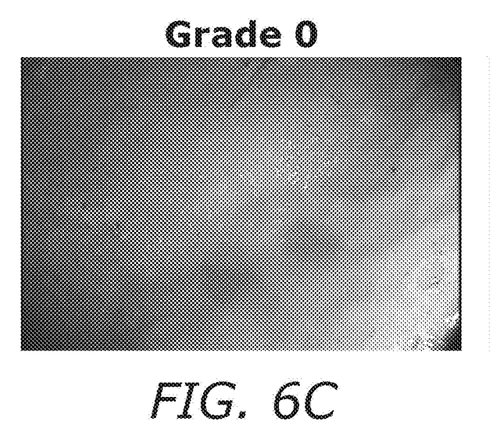
Figure 6D:
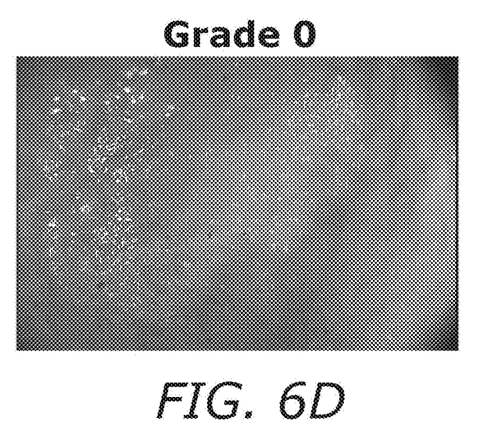

A 4 year old Thoroughbred Gelding was treated at a barn on the backside of Churchill Downs racetrack in Louisville, Ky. The horse was currently in training. The horse was treated with a composition including 2.2 gm/3 gm/10 mL of Omeprazole/fenbendazole each day during the treatment period. FIGS. 6A and 6B illustrate scopes of the horse's ulcer at initiation of treatment. FIGS. 6C and 6D illustrate re-scopes of the ulcerated area 14 days after initiation of treatment wherein the horse was clinically healed and its ulcer graded at zero.

Example 10

Horse Treatment

Figure 7A:
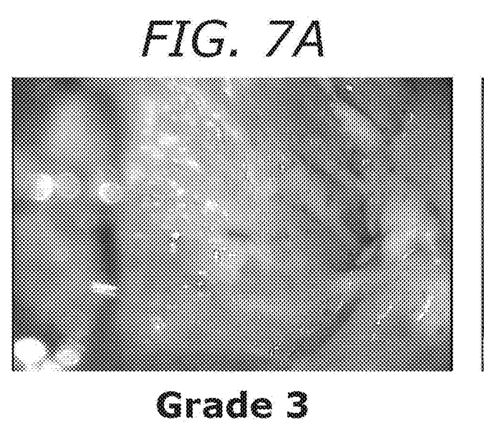
FIGS. 7A and 7B illustrate an ESDG in a second horse before treatment and FIGS. 7C and 7D illustrate a Grade 0 ESDG in the same horse after treatment.
Figure 7B:
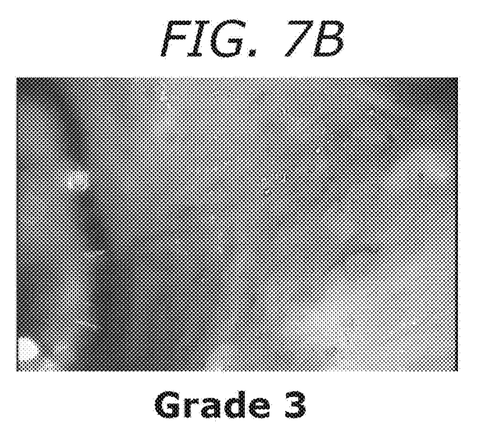
Figure 7C:
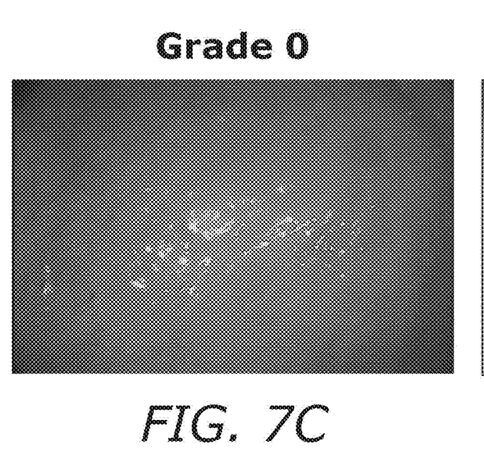
Figure 7D:
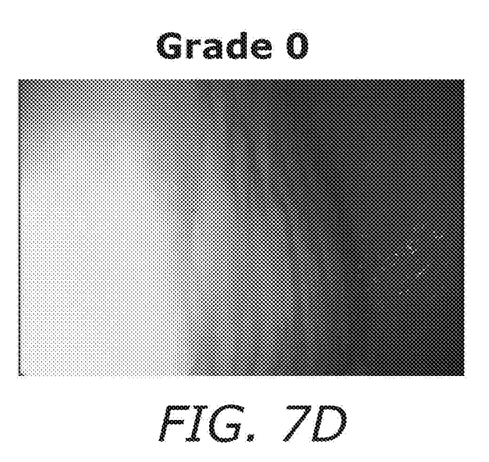

A 4 year old Thoroughbred Colt was treated at a barn on the backside of Churchill Downs racetrack in Louisville, Ky. This second horse was currently in training. The horse was treated with a composition including 2.2 gm/3 gm/10 mL of Omeprazole/ fenbendazole each day during the treatment period. FIGS. 7A and 7B illustrate scopes of the horse's ulcer at initiation of treatment. This second horse ran (raced) during treatment without adverse effects. FIGS. 7C and 7D illustrate re-scopes of the ulcerated area 14 days after initiation of treatment wherein the horse was clinically healed and its ulcer graded at zero.

Example 11

Horse Treatment

Figure 8A:
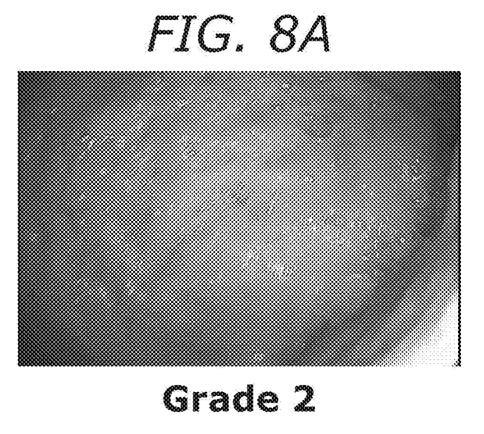
FIGS. 8A and 8B illustrate an ESDG in a third horse before treatment and FIGS. 8C and 8D illustrate a Grade 0 ESDG in the same horse after treatment.
Figure 8B:
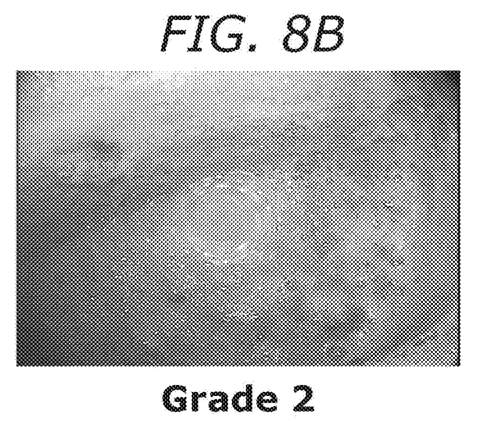
Figure 8C:
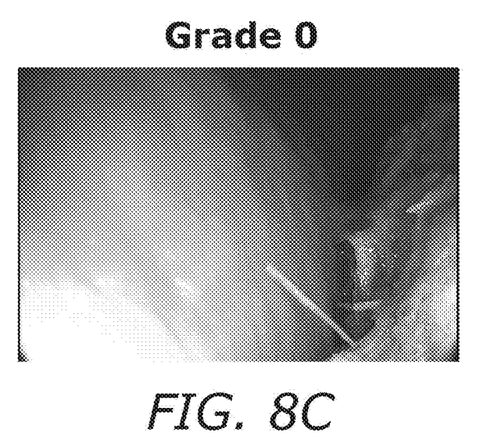
Figure 8D:
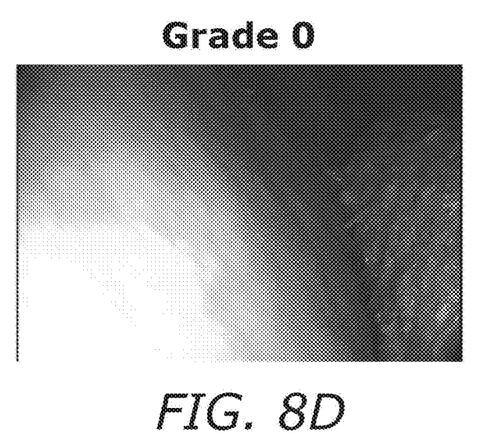

A 3 year old Thoroughbred Colt was treated at a barn on the backside of Churchill Downs racetrack in Louisville, Ky. The horse was currently in training. The horse was treated with a composition including 2.2 gm/3 gm/10 mL of Omeprazole/fenbendazole each day during the treatment period. FIGS. 8A and 8B illustrate scopes of the horse's ulcer at initiation of treatment. FIGS. 8C and 8D illustrate re-scopes of the ulcerated area 14 days after initiation of treatment wherein the horse was clinically healed and its ulcer graded at zero.

Example 12

Horse Treatment

A 3 year old, California bred Chestnut Filly is treated at a barn in Del Mar, Calif. The horse currently trains and exhibits a Grade 3 ulcer. The horse is treated with a paste composition including 2.2 gm/3 gm/10 mL of Omeprazole/ fenbendazole each day during the treatment period. After initiation of treatment, this horse wins a race at Del Mar, despite not being able to win prior to treatment.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A composition, including: a blended mixture including about 22% w/v omeprazole, about 30% w/v fenbendazole, and dextrose anhydrous powder.

2. The composition of claim 1, wherein the blended mixture includes granules.

3. The composition of claim 2, wherein the granules are provided as a scoop.

4. The composition of claim 3, wherein the scoop is 30 scoop.

5. The composition of claim 3, wherein the scoop is 60 scoop.

6. The composition of claim 3, wherein the scoop is 100 scoop.

7. A composition including:
a blended mixture including fenbendazole, carboxymethylcellulose, about 22% w/v omeprazole, and dextrose anhydrous powder, wherein the composition is formulated for oral administration.

8. The composition of claim 7, further including a wetting agent.

9. The composition of claim 7, further including sodium sulfite.

10. The composition of claim 7, further including sodium bicarbonate.

11. The composition of claim 7, further including a flavoring agent.

12. A composition including:
a blended mixture including omeprazole, carboxymethylcellulose, about 30% w/v fenbendazole, and dextrose anhydrous powder, wherein the composition is formulated for oral administration.

13. The composition of claim 12, further including a wetting agent.

14. The composition of claim 12, further including sodium sulfite.

15. The composition of claim 12, further including sodium bicarbonate.

16. The composition of claim 12, further including a flavoring agent.

* * * * *